(12) United States Patent
Lally et al.

(10) Patent No.: US 7,329,415 B2
(45) Date of Patent: Feb. 12, 2008

(54) MATERIALS CONTAINING MULTIPLE LAYERS OF VESICLES

(75) Inventors: John Martin Lally, Lilburn, GA (US); Nicholas Kotov, Stillwater, OK (US)

(73) Assignee: Novartis AG, Basel (CH)

( * ) Notice: Subject to any disclaimer, the term of this patent is extended or adjusted under 35 U.S.C. 154(b) by 732 days.

(21) Appl. No.: 10/387,190

(22) Filed: Mar. 12, 2003

(65) Prior Publication Data

US 2003/0219909 A1   Nov. 27, 2003

Related U.S. Application Data

(60) Provisional application No. 60/364,192, filed on Mar. 13, 2002.

(51) Int. Cl.
*A61K 9/00*    (2006.01)
*A61K 424/45*  (2006.01)

(52) U.S. Cl. .................. 424/429; 424/450; 623/6.59; 623/6.57

(58) Field of Classification Search .................. None
See application file for complete search history.

(56) References Cited

U.S. PATENT DOCUMENTS

| | | | | |
|---|---|---|---|---|
| 4,749,585 | A * | 6/1988 | Greco et al. | 428/422 |
| 5,208,111 | A | 5/1993 | Decher et al. | 428/420 |
| 6,001,556 | A | 12/1999 | Charych et al. | 435/5 |
| 6,022,748 | A | 2/2000 | Charych et al. | 436/527 |
| 6,103,217 | A | 8/2000 | Charych | 424/9.321 |
| 6,228,393 | B1 * | 5/2001 | DiCosmo et al. | 424/450 |
| 6,284,163 | B1 | 9/2001 | Stowell et al. | 264/4.1 |
| 6,819,244 | B2 * | 11/2004 | Dukler et al. | 340/572.1 |
| 6,936,298 | B2 * | 8/2005 | Chaikof et al. | 427/2.24 |
| 2001/0046564 | A1 | 11/2001 | Kotov | 427/430.1 |
| 2001/0048975 | A1 | 12/2001 | Winterton et al. | 427/412.1 |

FOREIGN PATENT DOCUMENTS

| | | |
|---|---|---|
| WO | WO 97/26870 | 7/1997 |
| WO | WO 99/08729 | 2/1999 |
| WO | WO 99/11122 | 3/1999 |
| WO | WO 99/47252 | 9/1999 |
| WO | WO 99/59649 | 11/1999 |
| WO | WO 00/44507 | 8/2000 |
| WO | WO 00/62830 | 10/2000 |
| WO | WO 01/07016 | 2/2001 |
| WO | WO 01/32230 | 5/2001 |
| WO | 01/49338 | * 7/2001 |
| WO | WO 01/49338 | 7/2001 |
| WO | WO 01/51196 | 7/2001 |
| WO | WO 01/72878 | 10/2001 |

OTHER PUBLICATIONS

International Search Report.
Biggs, Walker, & Kline, "The Formation of an Irreversibly Adsorbed and Organized Micelle Layer at the Solid-Liquid Interface", Jul. 22, 2002, Nano Letters 2002vvol. 2, No. 12, 1409-1412.

* cited by examiner

*Primary Examiner*—Gollamudi S. Kishore
(74) *Attorney, Agent, or Firm*—Sheng-Hsin Hu; Jian Zhou

(57) ABSTRACT

The present invention provides a composite material, preferably an ophthalmic device, more preferably a contact lens, which comprises a vesicle-containing coating including at least one layer of a vesicle and one layer of a polyionic material having charges opposite the charges of the vesicle. Such composite material can find use in biomedical applications, for example, a device for localized drug delivery and an in vivo analyte sensor such as glucose sensing contact lens. By lifting off the vesicle-containing coating from a substrate, a self-standing membrane (film) capable of encapsulating a wide variety of guest materials can be prepared. In addition, the invention provides methods for making vesicle-containing composite and film materials of the present invention.

3 Claims, 1 Drawing Sheet

MATERIALS CONTAINING MULTIPLE LAYERS OF VESICLES

This application claims the benefit under 35 U.S.C. § 119(e) of U.S. provisional application Ser. No. 60/364,192 filed Mar. 13, 2002, herein incorporated by reference in its entirety.

This invention relates to materials comprising one or more layers of vesicles, such as liposomes including polymerized liposomes and liposomes stabilized by a shell of inorganic silicate or polyelectrolytes or the like, polymerized micelles, and micro- and nano-capsules coated with polyelectrolytes. The material of the invention can carry a wide variety of guest materials having different functions and may find particular use in various biomedical applications, such as drug delivery, in vivo sensors, and gene therapy. In addition, this invention relates to a method for producing such materials containing multiple layers of vesicles.

BACKGROUND

Liposomes are microscopic vesicles, which are generally spherical and have diameters ranging from about 25 to about 30,000 nm. They have concentric lipid bilayer structures consisting of closed concentric lamellae enclosing one or more aqueous-containing compartments. Liposomes are formed from lipid or lipid-like molecules having a lipophilic and hydrophilic moiety and can encapsulate various materials including biologically active materials and are widely used in drug delivery. Recent research has found that some liposomes can also perform as sensitive sensors for the detection of various analytes (see, e.g., Reichert et al., J. Am. Chem. Soc. 117:829 (1995); Spevak et al., J. Am. Chem. Soc. 115:1146 (1993); Charych et al., Science 261:585 (1993); and U.S. Pat. No. 6,103,217). Typically, liposomes are used in liquid, paste, creme, gel, and lotion formulations. To date, liposomes are rarely used in an implantable device for localized drug delivery within a human body, partly because solid-state materials containing intact liposomes are difficult to make or not biocompatible and partly because liposomes are difficult to be immobilized to the surface of a substrate. A few methods have been developed that overcome some of the difficulties by employing polysacharides and biocompatible acrylate gels to encapsulate liposomes. Those methods have some shortcomings such as low liposome entrapment volume, the inability to immobilize preformed liposomes, and material instability at elevated temperatures. Recently, it is reported that liposomes can be immobilized in sol-gel glass by using sol-gel technology (U.S. Pat. No. 6,022,748 and PCT publication No. WO 97/26870). Liposome-containing sol-gel materials may offer the advantages of chemical and physical stabilization of the liposomes and allowing facile handling, and the opportunity of recovery and reuse. However, liposome-containing sol-gel materials may not be suitable for making medical devices such as ophthalmic lenses and implantable drug delivery device.

Thus, there is need for a material which comprise immobilized vesicles and is suitable for making a medical device (preferably an ophthalmic lens), an implantable device for localized drug delivery, or an in vivo biosensor. Such material can be easily tailored to entrap guest materials within a medical device or to delivery therapeutic agents at a localized site within a human body.

One object of the invention is to solve the above-mentioned difficulties in immobilizing liposomes and other vesicles to the surface of a solid-state material.

Another object of the invention is to provide a method for making a vesicle-containing material suitable for making a medical device.

A further object of the invention is to provide a vesicle-containing material that can carry a wide variety of guest materials having different functions and can find use in various biomedical applications, such as drug delivery, implantable sensors, and gene therapy.

A still further object of the invention is provide a medical device that contain vesicles carrying desired guest materials.

SUMMARY OF THE INVENTION

This invention is partly based on discoveries that vesicles with a charged surface, such as liposomes, polymerized micelles, and micro- and nano-capsules coated with polyelectrolytes, can be immobilized to the surface of a substrate by using a cost-effective coating process, a layer-by-layer (LbL) coating process. One or more bilayers, consisting of one layer of a vesicle with a charged surface and one layer of a polyelectrolyte having charges opposite the charges of the vesicle, can be deposited onto the surface of a substrate. This can be done by alternatively dipping the substrate in a polyelectrolyte solution and a vesicle dispersion or by alternatively spraying the substrate with a polyelectrolyte solution and a vesicle dispersion. The number of the deposition cycles regulates the thickness of the coating formed on the substrate and therefore the level/quantity of entrapped vesicles. By using a LbL coating process, a composite material can be produced to comprise a bulk material and a vesicle-containing coating capable of encapsulating a wide variety of guest material having different functions. Such composite material can find use in biomedical applications, for example, a device for localized drug delivery and an in vivo analyte sensor such as glucose sensing contact lens. By lifting off the vesicle-containing coating from the substrate, a self-standing membrane (film) capable of encapsulating a wide variety of guest materials can be prepared. The present invention can provide solid-state materials that have high capacities for encapsulating a wide variety of quest materials having different functions.

The invention, in one aspect, provides a composite material comprising a bulk material and a vesicle-containing coating capable of encapsulating guest materials, wherein vesicle-containing coating comprises at least one bilayer of a vesicle with a charged surface and a polyionic material having charges opposite the surface charges of the vesicle. The bulk material is preferably a polymeric article, more preferably a medical device, even more preferably an ophthalmic device, most preferably a contact lens.

The invention, in another aspect, provides a film of vesicle-containing material capable of encapsulating guest materials, comprising at least one bilayer of a vesicle with a charged surface and a polyionic material having charges opposite the surface charges of the vesicle.

The invention, in a further aspect, provides a method of making a composite material comprising a bulk material and a vesicle-containing coating capable of encapsulating guest materials. The method of the invention comprises: alternatively applying, in no particular order, one layer of a vesicle with a charged surface and one layer of a polyionic material having charges opposite the charges of the vesicle, onto the surface of the bulk material.

The invention, in a still further aspect, provides a method of making a film of vesicle-containing material capable of encapsulating guest materials. The method of the invention comprises: (1) forming a film on a substrate by depositing a plurality of bilayers of a vesicle with a charged surface and a polyionic material having charges opposite the surface charges of the vesicle onto the surface of the substrate and (2) lifting off the film from the substrate.

These and other aspects of the invention will become apparent from the following description of the presently preferred embodiments. The detailed description is merely illustrative of the invention and does not limit the scope of the invention, which is defined by the appended claims and equivalents thereof. As would be obvious to one skilled in the art, many variations and modifications of the invention may be effected without departing from the spirit and scope of the novel concepts of the disclosure.

DETAILED DESCRIPTION OF THE PREFERRED EMBODIMENTS

Figure 1:
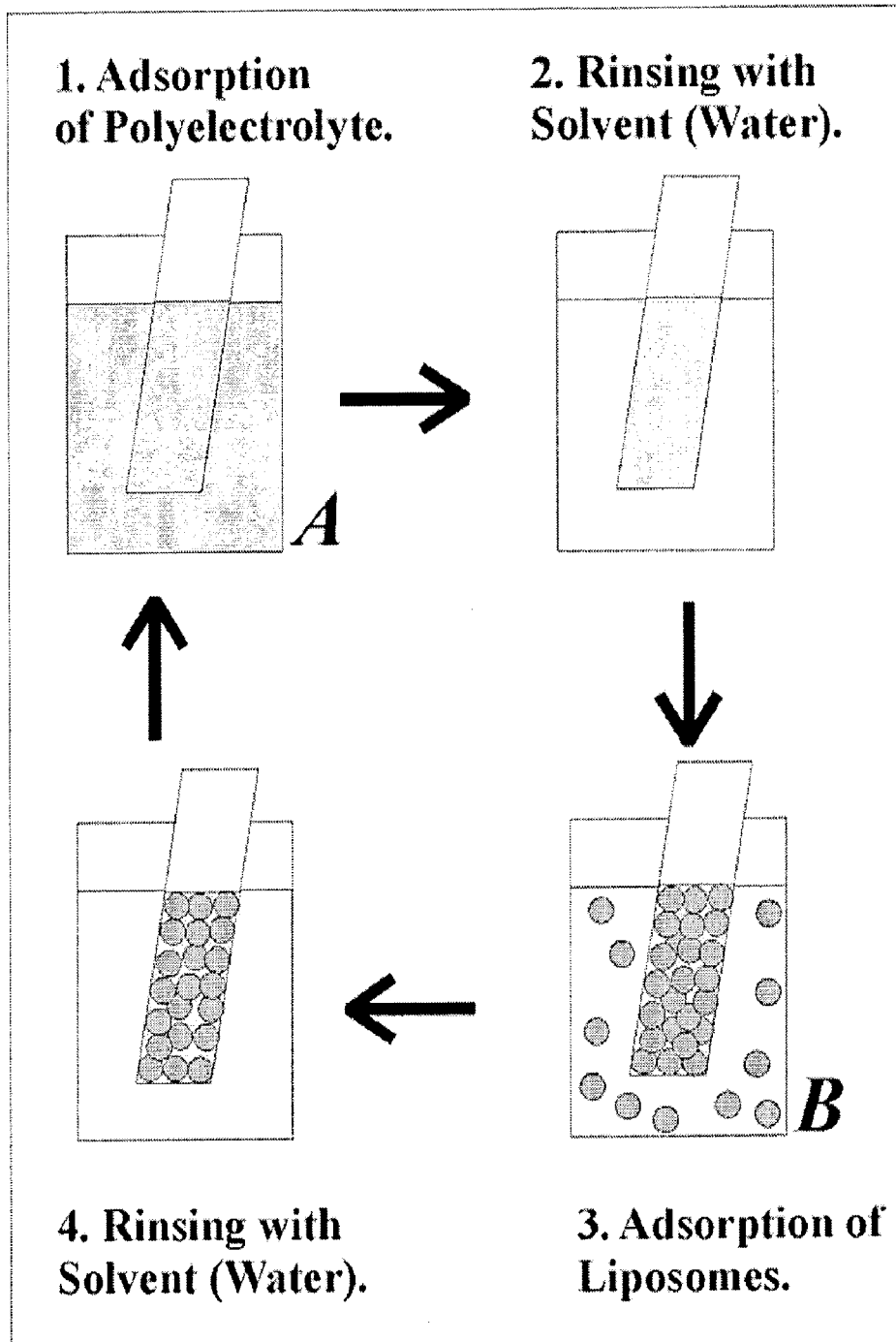
FIG. 1 shows schematically layer-by-layer deposition of vesicles with surface charges according to a preferred embodiment of the invention.

Reference now will be made in detail to the embodiments of the invention, one or more examples of which are set forth below. Each example is provided by way of explanation of the invention, not limitation of the invention. In fact, it will be apparent to those skilled in the art that various modifications and variations can be made in the present invention without departing from the scope or spirit of the invention. For instance, features illustrated or described as part of one embodiment, can be used on another embodiment to yield a still further embodiment. Thus, it is intended that the present invention cover such modifications and variations as come within the scope of the appended claims and their equivalents. Other objects, features and aspects of the present invention are disclosed in or are obvious from the following detailed description. It is to be understood by one of ordinary skill in the art that the present discussion is a description of exemplary embodiments only, and is not intended as limiting the broader aspects of the present invention.

Unless defined otherwise, all technical and scientific terms used herein have the same meaning as commonly understood by one of ordinary skill in the art to which this invention belongs. Generally, the nomenclature used herein and the laboratory procedures are well known and commonly employed in the art. Conventional methods are used for these procedures, such as those provided in the art and various general references. Where a term is provided in the singular, the inventors also contemplate the plural of that term. The nomenclature used herein and the laboratory procedures described below are those well known and commonly employed in the art.

In one embodiment, the present invention provides a composite material having a bulk material and a coating capable of encapsulating guest materials, wherein the coating comprises one or more bilayers of a vesicle with a charged surface and a polyionic material having charges opposite the charges of the vesicle.

For the purpose of this invention the term "bulk material" is intended to cover any self-standing material having a desired shape. In accordance with the invention, a bulk material can be polymeric materials, metals, glass, ceramics, or quartz. Exemplary polymeric materials include, but are not limited to, hydrogels, silicone-containing hydrogels, polymers and copolymers of styrene and substituted styrenes, ethylene, propylene, acrylates and methacrylates, N-vinyl lactams, acrylamides and methacrylamides, acrylonitrile, acrylic and methacrylic acids. A bulk material can also be an article, preferably an ophthalmic device, a mold for making an ophthalmic device, or a medical device other than ophthalmic device.

A "medical device", as used herein, refers to a device having surfaces that contact tissue, blood, or other bodily fluids of patients in the course of their operation or utility. Exemplary medical devices include: (1) extracorporeal devices for use in surgery such as blood oxygenators, blood pumps, blood sensors, tubing used to carry blood and the like which contact blood which is then returned to the patient; (2) prostheses implanted in a human or animal body such as vascular grafts, stents, pacemaker leads, heart valves, and the like that are implanted in blood vessels or in the heart; (3) devices for temporary intravascular use such as catheters, guide wires, and the like which are placed into blood vessels or the heart for purposes of monitoring or repair; (4) artificial tissues such as artificial skin for burn patients; (5) dentifices, dental moldings; (6) ophthalmic devices; and (7) cases or containers for storing ophthalmic devices or ophthalmic solutions. In a preferred embodiment, medical devices are ophthalmic devices.

An "ophthalmic device", as used herein, refers to a contact lens (hard or soft), an intraocular lens, a corneal onlay, and other ophthalmic devices (e.g., stents, glaucoma shunt, or the like) used on or about the eye or ocular vicinity.

The term "bilayer" is employed herein in a broad sense and is intended to encompass, a coating structure formed by applying first one layer of a first coating material and then one layer of a second coating material having charges opposite the charges of the first coating material. In accordance with this invention, a bilayer of a vesicle and a polyionic material having charges opposite the charges of the vesicles consists of one layer of the vesicle and one layer of the polyionic material. It should be understood that the layers of the first (e.g., a vesicle) and second (e.g., a polyionic material) coating materials may be intertwined with each other in the bilayer.

In accordance with the present invention, vesicles include liposomes, polymerized micelles, and nanocapsules and microcapsules each having a multilayered shell of polyelectrolytes.

Liposomes are microscopic vesicles having a concentric lipid bilayer structure consisting of closed concentric lamellae enclosing one or more aqueous-containing compartments. Liposomes are generally spherical and prepared from lipids or lipid-like molecules of general formula XY, wherein X is a polar hydrophilic group and Y is a non-polar hydrophobic group. The lipid or lipid-like molecules are normally arranged in a bilayer formation, similar to the lipid arrangement of biological membranes. Typically, the polar end (X) of a lipid or lipid-like molecule is in contact with the surrounding solution, usually aqueous solution, while the non-polar, hydrophobic end (Y) of the lipid or lipid-like molecule is in contact with the non-polar, hydrophobic end of another lipid or lipid-like molecule. The resulting bilayer membrane is selectively permeable to molecules of a certain size, hydrophobicity, shape, and net charge.

Liposomes can be divided into three categories based on their overall size and the nature of the lamellar structure. To describe these physical classifications, the nomenclature developed at the New York Academy of Sciences meeting on "Liposomes and Their Use in Biology and Medicine," of September 1977 will be used. The three classifications are multilamellar vesicles (MLV), small unilamellar vesicles (SUV) and large unilamellar vesicles (LUV). Small unilamellar vesicles range in diameter from approximately 200 to 500 nm and consist of a single lipid bilayer surrounding an aqueous compartment. A particular characteristic of SUV's is that a large amount about 70%, of the total lipid is located in the outer layer of the vesicle. In addition, the small radius of curvature imposes strain in packing of the lipid molecules resulting in them being rendered metastable in certain circumstances. The most frequently encountered and easily prepared liposomes are multilamellar vesicles (MLV). MLV vary greatly in size up to about 10,000 nm and are multi-compartmental in their structure. Large unilamellar vesicles (LUV) have a diameter ranging from about 600 nm to about 30 microns. Such vesicles may contain one or more bilayers.

The liposomes may be anionic (negatively-charged surfaces), basic (positively-charged surface) or neutral depending upon the choice of hydrophilic groups. For instance when a phosphate or a sulfate group is used as the polar group (X) the resulting liposome will be anionic. When amino-containing lipids or lipid-like molecules are used the liposomes will have a positive charge, or be cationic liposomes; and when polyethyleneoxy or glycol groups are present in the lipids or lipid-like molecules, neutral liposomes will be obtained. It should be understood that the neutral liposomes can be modified chemically or physically to have superficial charges. For example, neutral liposomes can be coated with polyelectrolytes.

Lipids or lipid-like compounds suitable for forming liposomes can be found in the following references: McCutcheon's Detergents and Emulsifiers and McCutcheon's Functional Materials, Allured Pub. Company, Ridgewood, N.J., U.S.A. Exemplary lipids or lipid-like compounds include lecithin, phosphatidyl ethanolamine, lysolecithin, lysophosphatidylethanolamine, phosphatidylserine, phosphatidyl inositol, sphingomyelin, cephalin, cardiolipin, phosphatidic acid, cerebrosides, dicetyl-phosphate, phosphatidyl-choline and dipalmitoyl-phosphatidylcholine. Additional, non-phosphorous-containing lipids are for instance, stearylamine, dodecylamine, hexadecylamine, cetyl palmitate, glyceryl ricinoleate, hexadecyl stearate, isopropyl myristate, amphoteric acrylic polymers, triethanolamine-lauryl sulphate, alcoyl-aryl sulfonates, polyethoxylated fatty acid amides and the like.

Liposomes can be prepared by methods known to those of skill in the art (see, e.g., Kim et al. Bioch. Bioph. Acta 728:339-348 (1983); Assil et al. Arch Ophthalmol. 105:400 (1987); Szoka & Papahadjopoulos, Ann. Rev. Biophys. Bioeng., 9:467-508 (1980); and U.S. Pat. No. 4,522,811, and other citations herein and known to those of skill in the art). For the practitioner of this invention who may wish to precisely control the number of layers and vesicle size of the liposomes employed, that person is referred to reviews by Pagano and Weinstein (Ann. Rev. Biophysic. Bioeng., 7, pp. 435-68 (1978)) and Szoka and Papahadjopoulos (Ann. Rev. Biophysic. Bioeng., 9, pp. 467-508 (1980)) and to a number of patents for preparing liposomes such as, for example, U.S. Pat. Nos. 4,229,360; 4,224,179; 4,217,344; 4,241,046; 4,078,052 and 4,235,871, all of which are hereby incorporated by reference.

Various additives can be combined with the lipids or lipid-like materials so as to modify the permeability and/or superficial charges of liposomes. Representative additives include long chain alcohols and diols; sterols, for example, cholesterol; long chain amines and their quaternary ammonium derivatives; dihydroxyalkylamines; polyoxyethylenated fatty amines; esters of long chain amino alcohols, their salts and quaternary ammonium derivatives; phosphoric esters of fatty alcohols, for example, sodium dicetyl phosphate; alkysulfates, for example, sodium cetyl sulfate; certain polymers such as polypeptides; and proteins.

Liposomes may be designed and prepared to respond to a specific stimulus, or combination of stimuli, as well as to have a particular stability, rigidity, and permeability. Exemplary stimuli include, but are not limited to, pH, temperature, light, detergents, metal ions, and the like.

Seki et al., in "Polym. Materials Sciences and Eng.", Proc. of ACS Div. of Polym. Materials Meeting in Philadelphia, Pa., ACS, 51, 216-219 (1984), disclose pH-dependent release of the guest materials encapsulated in liposome formed from egg yolk phosphatidyl choline. Seki et al. used a synthetic poly(carboxylic acid), poly(alphaethylacrylic acid) PEAA to effect a pH-dependent release of the encapsulated guest materials. Phosphatidyl choline vesicles are unaffected by PEAA at high pH but are rendered unstable at pH 7 or below.

Pidgeon and Hunt, in "Light Sensitive Liposomes" in Photochem and Photobiol. 37, 491-494 (1983), described liposomes having a permeability which can be changed by irradiation with UV light. Pidgeon and Hunt used two photosensitive phospholipids, 1,2-diretinoyl-Sn-glycero-3-phosphocholine and 1-palmitoyl,2-retinoyl-Sn-glycero-3-phosphocholine, in their studies. The permeability of liposomes formed from either or both of these phospholipids is directly proportional to temperature. Upon exposure to 30 to 120 seconds of 360 nm light, the permeability of the liposomes increases dramatically, from approximately 20% to almost 90%.

Kano et al., in Photochem. Photobiol. 34, 323-325 (1981) and Chem. Lett. 421-424 (1981), disclosed different photosensitive liposomes. Kano et al showed that incorporation of light isomerizable azobenzene lipids into liposome membranes produces vesicles with increased membrane permeability upon exposure to light.

The sensitivity of liposomes to temperature is also well known. This is largely based on the gel-liquid crystal transition temperature (Tc or Tm) of lipids that form liposomes. A specific lipid composition may be formulated so that the transition temperature is above the temperature at which the liposomes are to encapsulate guest materials yet low enough to allow for release when the temperature is raised slightly.

Phospholipase is able to cleave one or more of the phospholipids making up liposomes. Therefore, the liposomes formed from phospholipids may be destabilized using phospholipase enzymes so as to release guest materials encapsulated in the liposomes.

Bivalent metals have also been shown by D. Papahadjopoulos and J. C. Watkins in Biochem. Biophys. Acta. 135, 639-652 (1967) to increase the permeability of liposomal bilayers.

Any method known to a person skilled in the art for preparing liposomes whose stability or permeability can be significantly altered by manipulation of the immediate environment, either in vivo or in vitro, may be used in the present invention.

In a preferred embodiment of the invention, liposomes are stabilized by a shell of polyelectrolytes or inorganic silica or the like. In another preferred embodiment of the invention, liposomes are stabilized by forming polymerized liposomes. Stabilized liposomes may facilitate handling of liposomes in LbL coating process.

For controlled release of guest materials from liposomes stabilized by a shell of polyelectrolytes, it is preferable that the polyelectrolytes are biodegradable or photo-degradable.

A number of methods for preparing polymerized liposomes have been disclosed in the prior art (see, for example, U.S. Pat. No. 6,187,335; PCT International Publication WO 9503035; Chen et al., 1995, Proceed. Internat. Symp. Control. Rel. Bioact. Mater. 22; Chen et al., 1995 Proc. 3rd U.S. Japan Symposium on Drug Delivery Systems; Brey, R. N., 1997, Proc. 4th U.S. Japan Symposium on Drug Delivery; all of which are herein incorporated by reference in their entirety). A number of compounds have been disclosed in the prior art to be able to form polymerized liposomes (see, for example, U.S. Pat. Nos. 4,248,829; 4,485,045; 4,808,480; 4,594,193; 5,160,740; 5,466,467; 5,366,881; Regen, in Liposomes: from Biophysics to Therapeutics (Ostro, ed., 1987), Marcel Dekker, N.Y.; Singh, A., and J. M. Schnur, 1993, "Polymerizable Phospholipids", in Phospholipids Handbook, Gregor Cevc, ed., Marcel Dekker, New York; all of which are herein incorporated by reference in their entirety.

Polymerized liposomes which entrap guest materials can be prepared by any method known to a person skilled in the art. For example, liposomes are first formed according to one of the above-described methods known to a person skilled in the art, to encapsulate a guest material. Then, such preformed liposomes with guest materials encapsulated therein are polymerized by photopolymerization or thermal polymerization.

Micelles are dynamic aggregates formed in a polar solvent such as water from surfactants, molecules having both hydrophilic and hydrophobic groups. A micelle typically takes roughly the shape of a sphere, a spheroid, an ellipsoid, or a rod, with the hydrophilic groups on the exterior and the hydrophobic groups on the interior. The hydrophobic interior provides, in effect, a hydrophobic liquid phase with solvation properties differing from those of the surrounding solvent. Micelles form when the surfactant concentration in solution is greater than a characteristic value known as the critical micelle concentration ("CMC").

Polymerized micelles, or polymerized surfactant aggregates, were first developed in the late 1970's and early 1980's. Compared to otherwise identical non-polymerized micelles ("conventional micelles"), polymerized micelles exhibit enhanced stability and better control over micelle size. An important advantage of polymerized micelles is that they have no critical micelle concentration ("CMC"). A number of methods for preparing polymerized micelles have been disclosed in the prior art (see, for example, C. Palmer et al., J. High Res. Chromatogr., vol. 15, pp. 756-762 (1992); C. Larrabee et al., J. Poly. Sci.: Poly. Lett. Ed., vol. 17, pp. 749-751 (1979); D. Tabor et al., Chromatogr., vol. 20, pp. 73-80 (1989); S. Terabe et al., Anal. Chem., vol. 62, pp. 650-652 (1990); and J. Fendler et al., Acc. Chem. Res., vol. 17, pp. 3-8 (1984).

"Guest materials" as used herein refer to any materials which are associated with or entrapped in or bound to a vesicle. Exemplary guest materials include, without limitation, materials that impart desired functionalities to a medical device, for example, fluorescently labeled glucose receptor and the fluorescently labeled glucose competitor in ocular glucose sensors disclosed in March's PCT International Publication WO 01/13783, biosensor, drugs, proteins (such as enzymes or hormones or the likes), amino acids, nucleic acids, polypeptides, metallic nanoparticles, magnetic nanoparticles, optically active nanoparticles, dyes, and the like.

As used herein, the term "biosensors" refers to any sensor device or system that is partially or entirely composed of biological molecules (such as enzymes, antibodies, whole cells, organelles, or combinations thereof).

As used herein the term "drugs" includes medicaments, therapeutics, vitamins, nutritional supplements, and the like. If the guest material is a drug, it is present in therapeutically effective amounts relative to its function.

Any pharmaceutical drug can be utilized such as, for example, anti cancer drugs, drug for central nerves, drugs for peripheral nerve, drugs for allergy, drugs for circulatory organs, drugs for respiratory organs, drugs for digestive organs, hormone drugs, antibiotics, drugs for chemotherapy, vitamins, food supplements and the like.

Guest materials, such as drugs, can be encapsulated by vesicles or associated with or covalently linked to vesicles and then released from the medical device once it is in contact with a body fluid. If the drug is covalently linked to the vesicles, it is released by enzymatic cleavage (hydrolysis). Alternatively, the encapsulated or associated drug is released from the vesicles after in contact with a body fluid.

As used herein, a "polyionic material" refers to a polymeric material that has a plurality of charged groups, such as polyelectrolytes, p- and n-type doped conducting polymers. Polyionic materials include both polycationic (having positive charges) and polyanionic (having negative charges) materials.

The polyionic materials that may be employed in the present invention include polyanionic and polycationic polymers. Examples of suitable polyanionic polymers include, for example, a synthetic polymer, a biopolymer or modified biopolymer comprising carboxy, sulfo, sulfato, phosphono or phosphato groups or a mixture thereof, or a salt thereof, for example, a biomedically acceptable salt and especially an ophthalmically acceptable salt thereof when the article to be coated is an ophthalmic device.

Examples of synthetic polyanionic polymers are: a linear polyacrylic acid (PAA), a branched polyacrylic acid, for example a Carbophil® or Carbopol® type from Goodrich Corp., a polymethacrylic acid (PMA), a polyacrylic acid or polymethacrylic acid copolymer, for example a copolymer of acrylic or methacrylic acid and a further vinylmonomer, for example acrylamide, N,N-dimethyl acrylamide or N-vinylpyrrolidone, a maleic or fumaric acid copolymer, a poly(styrenesulfonic acid) (PSS), a polyamido acid, for example a carboxy-terminated polymer of a diamine and a di- or polycarboxylic acid, for example carboxy-terminated Starburst™ PAMAM dendrimers (Aldrich), a poly(2-acrylamido-2-methylpropanesulfonic acid) (poly-(AMPS)), or an alkylene polyphosphate, alkylene polyphosphonate, carbohydrate polyphosphate or carbohydrate polyphosphonate, for example a teichoic acid.

Examples of polyanionic biopolymers or modified biopolymers are: hyaluronic acid, glycosaminoglycanes such as heparin or chondroitin sulfate, fucoidan, polyaspartic acid, poly-glutamic acid, carboxymethyl cellulose, carboxymethyl dextranes, alginates, pectins, gellan, carboxyalkyl chitins, carboxymethyl chitosans, sulfated polysaccharides.

A preferred polyanionic polymer is a linear or branched polyacrylic acid or an acrylic acid copolymer. A more preferred anionic polymer is a linear or branched polyacrylic acid. A branched polyacrylic acid in this context is to be understood as meaning a polyacrylic acid obtainable by polymerizing acrylic acid in the presence of suitable (minor) amounts of a di- or polyvinyl compound.

A suitable polycationic polymer as part of the bilayer is, for example, a synthetic polymer, biopolymer or modified biopolymer comprising primary, secondary or tertiary amino groups or a suitable salt thereof, preferably an ophthalmically acceptable salt thereof, for example a hydrohalogenide such as a hydrochloride thereof, in the backbone or as substituents. Polycationic polymers comprising primary or secondary amino groups or a salt thereof are preferred.

Examples of synthetic polycationic polymers are:

(i) a polyallylamine (PAH) homo- or copolymer, optionally comprising modifier units;
(ii) a polyethyleneimine (PEI);
(iii) a polyvinylamine homo- or copolymer, optionally comprising modifier units;
(iv) a poly(vinylbenzyl-tri-$C_1$-$C_4$-alkylammonium salt), for example a poly(vinylbenzyl-tri-methyl ammoniumchloride);
(v) a polymer of an aliphatic or araliphatic dihalide and an aliphatic N,N,N',N'-tetra-$C_1$-$C_4$-alkyl-alkylenediamine, for example a polymer of (a) propylene-1,3-dichloride or -dibromide or p-xylylene dichloride or dibromide and (b) N,N,N',N'-tetramethyl-1,4-tetramethylene diamine;
(vi) a poly(vinylpyridine) or poly(vinylpyridinium salt) homo- or copolymer;
(vii) a poly (N,N-diallyl-N,N-di-$C_1$-$C_4$-alkyl-ammoniumhalide) comprising units of formula

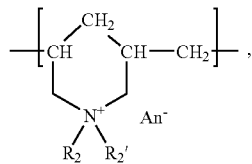

wherein $R_2$ and $R_2'$ are each independently $C_1$-$C_4$-alkyl, in particular methyl, and $An^-$ is an anion, for example, a halide anion such as the chloride anion;
(viii) a homo- or copolymer of a quaternized di-$C_1$-$C_4$-alkyl-aminoethyl acrylate or methacrylate, for example a poly (2-hydroxy-3-methacryloylpropyltri-$C_1$-$C_2$-alkylammonium salt) homopolymer such as a a poly(2-hydroxy-3-methacryloylpropyltri-methylammonium chloride), or a quaternized poly(2-dimethylaminoethyl methacrylate or a quaternized poly(vinylpyrrolidone-co-2-dimethylaminoethyl methacrylate);
(ix) POLYQUAD® as disclosed in EP-A-456,467; or
(x) a polyaminoamide (PAMAM), for example a linear PAMAM or a PAMAM dendrimer such as an amino-terminated Starburst™ PAMAM dendrimer (Aldrich).

The above mentioned polymers comprise in each case the free amine, a suitable salt thereof, for example a biomedically acceptable salt or in particular an ophthalmically acceptable salt thereof, as well as any quaternized form, if not specified otherwise.

Suitable comonomers optionally incorporated in the polymers according to (i), (iii), (vi) or (viii) above are, for example, hydrophilic monomers such as acrylamide, methacrylamide, N,N-dimethyl acrylamide, N-vinylpyrrolidone and the like.

Suitable modifier units of the polyallylamine (i) are known, for example from WO 00/31150 and comprise, for example, units of formula

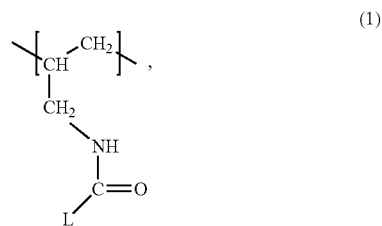

wherein L is $C_2$-$C_6$-alkyl which is substituted by two or more same or different substituents selected from the group consisting of hydroxy, $C_2$-$C_5$-alkanoyloxy and $C_2$-$C_5$-alkylamino-carbonyloxy.

Preferred substituents of the alkyl radical L are hydroxy, acetyloxy, propionyloxy, methylaminocarbonyloxy or ethylaminocarbonyloxy, especially hydroxy, acetyloxy or propionyloxy and in particular hydroxy.

L is preferably linear $C_3$-$C_6$-alkyl, more preferably linear $C_4$-$C_5$-alkyl, and most preferably n-pentyl, which is in each case substituted as defined above. A particularly preferred radical L is 1,2,3,4,5-pentahydroxy-n-pentyl.

Examples of polycationic biopolymers or modified biopolymers that may be employed in the bilayer of the present invention include: basic peptides, proteins or glucoproteins, for example, a poly-ε-lysine, albumin or collagen, aminoalkylated polysaccharides such as a chitosan or aminodextranes.

Particular polycationic polymers for forming the bilayer of the present invention include a polyallylamine homopolymer; a polyallylamine comprising modifier units of the above formula (1); a polyvinylamine homo- or -copolymer or a polyethyleneimine homopolymer, in particular a polyallylamine or polyethyleneimine homopolymer, or a poly (vinylamine-co-acrylamid) copolymer.

The foregoing lists are intended to be exemplary, but clearly are not exhaustive. A person skilled in the art, given the disclosure and teaching herein, would be able to select a number of other useful polyionic materials.

In order to alter various characteristics of the coating, such as thickness, the molecular weight of the polyionic materials can be varied. In particular, as the molecular weight is increased, the coating thickness generally increases. However, if the increase in molecular weight increase is too substantial, the difficulty in handling may also increase. As such, polyionic materials used in a process of the present invention will typically have a molecular weight $M_n$ of about 2,000 to about 150,000. In some embodiments, the molecular weight is about 5,000 to about 100,000, and in other embodiments, from about 75,000 to about 100,000.

Nano- and microcapsules having multilayered shell of polyionic materials can be prepared according to LbL encapsulation technologies disclosed in PCT patent application Nos. WO 99/47252 and WO01/51196. For example, microcapsules can be prepared by first charging a substance in a microcrystal form with an amphiphilic substance, followed by consecutively depositing polyionic materials of opposite charge to assembly a multilayered shell of polyionic materials around the microcrystal substance. The substance in a microcrystal form can be any substance to be encapsulated or a template. Where a template is used, the template can be removed from microcapsules with multilayered shell of polyionic materials by any known method, e.g., dissolving in a solvent, to form hollow capsules consisting of shells of polyionic materials. Such hollow capsules can encapsulate a wide range of materials including proteins. LbL encapsulation approach can be used to incorporate a wide range of entities including organic materials, inorganic materials, and biomaterials. By the number of layers of polyionic materials, by selecting the amphiphilic substance and polyionic materials used and by the conditions during coating with the amphiphilic substance the porosity of microcapsules can be tailored so as to have a desired permeability.

A composite material of the present invention can be prepared by using a layer-by-layer (LbL) coating process. LbL coating is based on the sequential adsorption of oppositely charged materials.

"LbL coating", as used herein, refers to a layer-by-layer ("LbL") alternative, physical deposition of two oppositely charged polymeric materials (polyionic materials) or of a vesicle with surface charges and a polyionic material having charges opposite of the charges of the vesicles on an article. The LbL coating of an article is not covalently bound to the core material of the article. In an LbL coating, each layer of a polyionic material is non-covalently bond to another layer of a different polyionic material or vesicle. Formation of an LbL coating on an article may be accomplished in a number of ways, for example, as described in U.S. Pat. No. 6,451,871 (herein incorporated by reference in its entirety) and pending U.S. patent applications (application Ser. Nos. 09/774942, 09/775104, 60/409,950), herein incorporated by reference in their entireties. One coating process embodiment involves solely dip-coating and dip-rinsing steps. Another coating process embodiment involves solely spray-coating and spray-rinsing steps. However, a number of alternatives involve various combinations of spray- and dip-coating and rinsing steps may be designed by a person having ordinary skill in the art.

LbL coatings can also be asymmetrical. As used herein, "asymmetrical coatings" on an ophthalmic lens refers to the different coatings on the first surface and the opposite second surface of the ophthalmic lens. As used herein, "different coatings" refers to two coatings that have different surface properties or functionalities.

FIG. 1 schematically illustrates a process for applying a vesicle-containing coating onto the surface of a substrate, according to one preferred embodiment of the present invention. Positively charged polyelectrolytes (PE), or positively charged species A, are readily adsorbed to the surfaces of glass, quartz, silica, metals and most other materials due to natural negative charge or existence of oxidation layer (step 1 in FIG. 1). Rinsing with water between the adsorption steps removes the excess of the previous solution and leaves a thin (mono)layer of A species on the surface (step 2 in FIG. 1). Electrostatic and van der Waals attraction between the layer of A and oppositely charged material B (e.g., vesicle) promotes its adsorption to the substrate (step 3 in FIG. 1). The rinsing (step 4 in FIG. 1) yields a thin (mono)layer of B, which makes it suitable for the adsorption of a new layer of component A. Then the cycle can be repeated as many times as necessary to reach the desirable thickness of the multilayers. The recurrent nature of the process makes it very attractive for both laboratory and industrial implementations. A and B are preferentially chosen to be of relatively high molecular weight. Van der Waals bonds strengthen with the increase of molecular mass and the multiple points of attachment of A and B render the absorption sufficiently irreversible to allow for the deposition of the next layer.

An LbL coating (film) obtained after n deposition cycles can be generically referred to as $(A/B)_n$. It is important to note that the $(A/B)_n$ abbreviation describes primarily the deposition procedure rather than the actual sequence of the multilayers obtained as a result of it. The films, where the adjacent layers deposited in one cycle can be clearly distinguished from each other, are difficult to obtain because of the strong interpenetration of chains of A and B blurring the border between the adjacent layers. In the majority of LbL pairs, the result of the LbL assembly can be characterized the best as a molecular blend of A and B.

The vesicles with negatively charged surface can be assembled with polycationic materials, while vesicles with positively charged surface can be assembled with polyanionic materials. The LbL coating of vesicle-containing materials can also be realized when chemical interactions specific for particular pairs of reagents are present between vesicles and their LbL partners. Specific affinity between partners can be imparted by the derivatization of one or both components with biospecific molecules, including but not limited to biotin, complementary DNAs, antibodies, antigens, and the like, structure-specific superficial interactions, including but not limited to molecularly imprinted surfaces, or coordination compounds, such as phenantrolin.

In the course of film build-up, the components of the film can be replaced with different ones. As well, the contents of the vesicles can be altered. This will lead to the multifunctional stratified materials.

A vesicle-containing coating of the invention can be formed on the a bulk material with or without surface modification.

"Surface modification", as used herein, refers to treating, functionalizing, or coating a bulk material to alter its surface properties, according to a known procedure prior to formation thereon of the vesicle-containing coating. For example, an article can be treated in a surface treatment process (or a surface modification process), in which, by means of contact with a vapor or liquid, and/or by means of application of an energy source (1) a coating is applied to the surface of an article, (2) chemical species are adsorbed onto the surface of an article, (3) the chemical nature (e.g., electrostatic charge) of chemical groups on the surface of an article are altered, or (4) the surface properties of an article are otherwise modified. Exemplary surface treatment processes include, but are not limited to, a surface treatment by energy (e.g., a plasma, a static electrical charge, irradiation, or other energy source), chemical treatments, the grafting of hydrophilic monomers or macromers onto the surface of an article, and layer-by-layer deposition of polyelectrolytes. A preferred class of surface treatment processes are plasma processes, in which an ionized gas is applied to the surface of an article. Plasma gases and processing conditions are described more fully in U.S. Pat. Nos. 4,312,575 and 4,632,844, which are incorporated herein by reference. The plasma gas is preferably a mixture of lower alkanes and nitrogen, oxygen or an inert gas. The surface modification of a contact lens includes, without limitation, the grafting of monomers or macromers onto polymers to make the lens biocompatible, deposit resistant, more hydrophilic, more hydrophobic, or the deposing of polyionic materials (LbL coating) to increase the lens hydrophilic properties or lubricity or to reduce bacterial adhesion or to impart antimicrobial or antifungal properties.

For example, the surface modification of a contact lens includes, without limitation, the grafting of monomers or macromers onto polymers to make the lens biocompatible, deposit resistant, more hydrophilic, more hydrophobic, or the deposing of polyionic materials (LbL coating) to increase the lens hydrophilic properties or lubricity or to reduce bacterial adhesion or to impart antimicrobial or antifungal properties.

For example, if the surface of a bulk material has hydroxy groups, the support may be placed in a bath of an innert solvent, such as tetrahydrofuran, and tresyl chloride. The hydroxy groups on the surface are then tresylated. Once tresylated, the surface may be aminated in a water solution of ethylene diamine, which results in bonding the group —NH—$CH_2$—$CH_2$—$NH_2$ to the carbon atom thereon. Alternatively, for example, a contact lens made from a hydrogel, can be dipped into or sprayed with a solution containing a diaziridine compound, which is subsequently attached covalently to the surface of the contact lens via a thermal process, so as to functionalize the contact lens. Such functionalized lenses can be used in covalently attaching guest materials or polyionic materials to the functionalized lens.

Once the desired coating is applied to a bulk material, the coating can, in some embodiments, be cross-linked to make the surface even more resistant to wear or abrasion, as well as more durable. The coating can generally be cross-linked by any method known in the art. For example, in one embodiment, a crosslinking agent can be sprayed onto the coating and, thereafter, radiation with visible light can then be applied such that the coating becomes cross-linked. Suitable crosslinking agents can include, for example, active moieties such as carbenes, nitrenes, and the like.

Vesicles may be coated with a shell of solid material, such as silicon oxide, to increase the stability of the vesicles, to improve encapsulation properties, and/or to increase affinity to polyionic materials in the vesicle-containing coating of the invention.

In a preferred embodiment, a vesicle-containing coating of the present invention comprises a plurality of bilayers of a vesicle with a charged surface and a polyionic material having charges opposite the charges of the vesicle. The vesicle-containing coating of the present invention preferably comprises 2-20 bilayers, even more preferably 2-6 bilayers, of a vesicle with a charged surface and a polyionic material having charges opposite the charges of the vesicle. If the vesicle-containing coating comprises multiple bilayers of a vesicle with a charged surface and a polyionic material having charges opposite the charges of the vesicle, a layer of polyionic materials having charges opposite the charges of the vesicle is sandwiched between two layers of the vesicle.

Preparation of a composite material comprising a bulk material and a vesicle-containing coating is another embodiment of the present invention. The method comprises: (a) contacting a bulk material with a dispersion of a vesicle selected from the group consisting of a liposome, a polymerized micelle, a nanocapsule having a multilayered shell of polyelectrolytes, and a microcapsule having a multilayered shell of polyelectrolytes to form a layer of the vesicle on the bulk material; (b) optionally rinsing said bulk material by contacting said bulk material with a rinsing solution; (c) contacting said bulk material with a solution of a polyionic material to form a layer of the polyionic material on top of the layer of the vesicle, wherein said polyionic material has charges opposite the charges of the vesicle; and (d) optionally rinsing said bulk material by contacting said bulk material with the rinsing solution.

Preferably, steps (a) to (d) are repeated for 2 to 10 times, provided that one layer of polyionic materials is sandwiched between each pair of neighboring layers of vesicle on the surface of the bulk material. More preferably, steps (a) to (d) are repeated for 2 to 6 times, provided that one layer of polyionic materials is sandwiched between each pair of neighboring layers of vesicle on the surface of the bulk material of the invention.

Where a composite material of the invention is a drug delivery device, the rate of guest material release can be controlled by utilizing multilayers of vesicle. The more vesicle layers, the slower is the release of the guest material.

Application of a layer of vesicle may be accomplished as described herein below for polyionic materials, e.g., solely dip-coating and dip-rinsing steps, solely spray-coating and spray-rinsing steps, or various combinations of spray- and dip-coating and rinsing steps.

Application of an LbL coating may be accomplished in a number of ways as described in pending U.S. patent applications (application Ser. Nos. 09/005317, 09/774942, 09/775104), herein incorporated by reference in their entireties. One coating process embodiment involves solely dip-coating and dip-rinsing steps. Another coating process embodiment involves solely spray-coating and spray-rinsing steps. However, a number of alternatives involve various combinations of spray- and dip-coating and rinsing steps may be designed by a person having ordinary skill in the art.

It has been discovered and disclosed in U.S. Pat. No. 6,451,871 that complex and time-consuming pretreatment of a bulk material (medical device) is not required prior to binding of a polyionic material to the bulk material. By simply contacting a bulk material, for example, a contact lens, with one or more solutions each containing one or more polyionic materials, an LbL coating can be formed on a bulk material to modify its surface properties.

One dip-coating alternative involves the steps of applying a coating of a first polyionic material to a core material of a medical device by immersing said medical device in a first solution of a first polyionic material; rinsing the medical device by immersing the medical device in a rinsing solution; and, optionally, drying the medical device. This procedure can be repeated using a second polyionic material, with the second polyionic material having charges opposite the charges of the first polyionic material, in order to form a polyionic bilayer. This bilayer formation process may be repeated a plurality of times in order to produce a thicker LbL coating.

The immersion time for each of the coating and rinsing steps may vary depending on a number of factors. Preferably, immersion of the bulk material into the polyionic solution occurs over a period of about 1 to 30 minutes, more preferably about 2 to 20 minutes, and most preferably about 1 to 5 minutes. Rinsing may be accomplished in one step, but a plurality of rinsing steps can be quite efficient.

Another embodiment of the coating process involves a series of spray coating techniques. The process generally includes the steps of applying a coating of a first polyionic material to a bulk material with a first solution of a first polyionic material; rinsing the medical device by spraying the medical device with a rinsing solution; and optionally, drying the bulk material. Similar to the dip-coating process, the spray-coating process may be repeated with a second polyionic material, with the second polyionic material having charges opposite the charges of the first polyionic material.

The contacting of a bulk material with solution, either polyionic material or rinsing solution, may occur by a variety of methods. For example, a bulk material may be dipped into both solutions. One preferred alternative is to apply the solutions in a spray or mist form. Of course, various combinations may be envisioned, e.g., dipping the medical device in the polyionic material followed by spraying the rinsing solution.

The spray coating application may be accomplished via a number of methods. For example, a conventional spray coating arrangement may be used, i.e., the liquid material is sprayed by application of fluid, which may or may not be at elevated pressure, through a reduced diameter nozzle which is directed towards the deposition target.

Preferably, a spraying process is selected from the group consisting of an air-assisted atomization and dispensing process, an ultrasonic-assisted atomization and dispensing process, a piezoelectric assisted atomization and dispensing process, an electro-mechanical jet printing process, a piezo-electric jet printing process, a piezo-electric with hydrostatic pressure jet printing process, and a thermal jet printing process; and a computer system capable of controlling the positioning of the dispensing head of the spraying device on the ophthalmic lens and dispensing the coating liquid. Those spraying coating processes are described in U.S. application Ser. No. 60/312199, herein incorporated by reference in its entirety. By using such spraying coating processes, an asymmetrical coating can be applied to a medical device. For example, the back surface of a contact lens can be coated with a hydrophilic and/or lubricous coating material and the front surface of the contact lens can be coated with a vesicle-containing coating capable of detecting an analyte in a tear fluid. It is also possible to produce a coating on a contact lens, the coating having a functional pattern so as to provide simultaneously multiple benefits to a wearer.

In accordance with the present invention, polyionic material solutions can be prepared in a variety of ways. In particular, a polyionic solution of the present invention can be formed by dissolving the polyionic material(s) in water or any other solvent capable of dissolving the materials. When a solvent is used, any solvent that can allow the components within the solution to remain stable in water is suitable. For example, an alcohol-based solvent can be used. Suitable alcohols can include, but are not limited to, isopropyl alcohol, hexanol, ethanol, etc. It should be understood that other solvents commonly used in the art can also be suitably used in the present invention.

Whether dissolved in water or in a solvent, the concentration of a polyionic material in a solution of the present invention can generally vary depending on the particular materials being utilized, the desired coating thickness, and a number of other factors. However, it may be typical to formulate a relatively dilute aqueous solution of polyionic material. For example, a polyionic material concentration can be between about 0.001% to about 0.25% by weight, between about 0.005% to about 0.10% by weight, or between about 0.01% to about 0.05% by weight.

In general, the polyionic solutions mentioned above can be prepared by any method well known in the art for preparing solutions. For example, in one embodiment, a polyanionic solution can be prepared by dissolving a suitable amount of the polyanionic material, such as polyacrylic acid having a molecular weight of about 90,000, in water such that a solution having a certain concentration is formed. In one embodiment, the resulting solution is a 0.001M PAA solution. Once dissolved, the pH of the polyanionic solution can also be adjusted by adding a basic or acidic material. In the embodiment above, for example, a suitable amount of 1N hydrochloric acid (HCl) can be added to adjust the pH to 2.5.

Polycationic solutions can also be formed in a manner as described above. For example, in one embodiment, poly (allylamine hydrochloride) having a molecular weight of about 50,000 to about 65,000 can be dissolved in water to form a 0.001M PAH solution. Thereafter, the pH can also be adjusted to 2.5 by adding a suitable amount of hydrochloric acid.

In another embodiment, the present invention provides a film (membrane) of vesicle-containing material, which comprises at least one layer of a vesicle and one layer of a polyionic material having charges opposite the charges of the vesicle. The film of vesicle-containing material of the invention comprises preferably 2-50 layers of each of the vesicle and the polyionic material, more preferably 5-35 layers of each of the vesicle and the polyionic material, even more preferably 5-20 layers of each of the vesicle and the polyionic material.

In a preferred embodiment, the film of vesicle-containing material of the invention further comprises different vesicles or vesicles containing different guest materials having different functions.

The film of vesicle-containing material of the invention can be prepared by lifting-off the above-described vesicle-containing coating from a bulk material.

In another embodiment, the present invention provides a method for preparing a film of vesicle-containing material capable of encapsulating guest materials. The method of the invention comprises: (1) forming a film on a substrate by depositing a plurality of bilayers of a vesicle with a charged surface and a polyionic material having charges opposite the surface charges of the vesicle onto the surface of the substrate and (2) separating the film from the substrate.

Any method for separating a film from a substrate can be used. Preferred methods are those disclosed in a PCT patent publication No. WO 01/72878. A substrate can be removed by dissolving it in an organic solvent. For example, a silicon wafer or glass substrate can be partially or completely dissolved by HF. Alternatively, a substrate can be removed through other chemical treatment, heat treatment, pH change, ionic strength change, or other means suitable to achieve the appropriate separation. For example, where a film is connected a substrate through a special sacrificial stratum, which can be decomposed by a chemical or photochemical means.

The composite and the film material of the invention can find use in various biomedical applications such as drug delivery, in vivo sensors, and gene therapy.

One exemplary use is to use the composite material to make a contact lens which is capable of releasing lubricants to a contact lens surface in a controlled manner for improved comfort.

For example, a mucin-like material, e.g., polyglycolic acid, polylactides, collagen or gelatin, can be used as guest materials which can be released continously and slowly over extended period of time to the ocular surface of the eye for treating dry eye syndrome. The mucin-like material preferably is present in effective amounts.

Under normal conditions, ocular fluid forms a thin layer (tear film) approximately 7-10 micrometers thick that covers the corneal and conjunctival epithelium. This ultra thin layer provides a smooth optical surface to the cornea by abolishing minute surface irregularities of its epithelium, wets the surface of the corneal and conjuctival epithelium, thereby preventing damage to the epithelial cells, and inhibits the growth of microorganisms on the conjunctiva in the cornea by mechanical flushing.

The tear film normally includes a three layer structure. The outermost layer is a lipid layer derived from the secretions of the meibomian glands. This layer is thought to retard evaporation of the aqueous layer. The middle aqueous layer is provided by the major and minor lacrimal glands, and contains water-soluble substances. The innermost mucinous layer is composed of glycoprotein, mucin, and overlies the corneal and conjunctival epithelial cells. The epithelial cell membranes are composed of lipoproteins and thus generally hydrophobic. The mucin plays an important role in wetting the surface. Under normal conditions, mucin is provided by goblet cells of the conjunctiva and is also provided from the lacrimal gland.

When any of the tear film components is deficient, the tear film will break up, and dry spots will form on the corneal and the conjunctival epithelium. Deficiency of any of the three components (aqueous, mucin or lipid) may result in dryness of the eye.

When the contact lens containing the mucin-like material in mucin-like material in an effective amount is inserted into the eye, the mucin-like material is released continously from the contact lens into the eye over an extended period of time and wets the eye.

Another example is that antimicrobial agents may be encapsulated in vesicles-containing composite material for making a biomedical device. In this way, if the biomedical device contains an antimicrobial agent, the contamination of the biomedical device, e.g., contact lens or intraocular lens, by microbes, e.g., bacteria, is reduced relative to a contact lens wherein the antimicrobial agent is absent. The antimicrobial agent is present in an amount sufficient to retard and/or substantially prevent contamination by the microbe.

Another exemplary use is making of an in vivo sensor. For example, PCT International Publication WO 01/13783 discloses that ophthalmic lenses can comprise biomolecule-sensing guest materials and be used as ocular sensors for non-invasive or minimally invasive monitoring of analytes such as glucose. Such ocular sensors for glucose can be used to conveniently, non-invasively and frequently monitor blood glucose levels by determining glucose levels in an ocular fluid, such as tears, aqueous humor, or interstitial fluid, based on the correlation between the blood glucose concentration and the ocular glucose concentration, and whereby to achieve the tight control of blood glucose levels by managing food intake and the dosage and timing of insulin injection. Ocular analyte sensors disclosed by March in PCT International Publication WO 01/13783 can be one potentially useful non-invasive technology.

Ocular glucose sensors, disclosed by March in PCT International Publication WO 01/13783, comprise biosensors such as fluorescently labeled glucose receptor and/or the fluorescently labeled glucose competitor. By encapsulating in vesicles in a composite material for making ocular glucose sensors, the biosensors may be fully contained within the ocular glucose sensor so as to achieve the higher precision and better reproducibility of the ocular analyte sensors and/or to minimize any potential adverse effects of the biosensors on ocular health.

Furthermore, by using the composite material of the invention, biosensors such as fluorescently labeled glucose receptor and/or the fluorescently labeled glucose competitor need neither to be incorporated in formulations for making contact lenses nor to be immobilized with a component (e.g., pre-polymer) in the formulations or with formed lenses. The immbobilization approach may increase the complexity of the production of ocular analyte sensors and may also adversely affect the functionalities of the guest molecules and thereby the performance of the ocular analyte sensors. Therefore, production of ocular analyte sensors can be simplified and can be carried out in a large scale. First, conventional ophthalmic lenses can be produced in a mass production environment. Then, the produced ophthalmic lenses can be coated with a desired vesicle encapsulating a biosensor for a desired analyte to make ocular analyte sensor for that analyte.

The previous disclosure will enable one having ordinary skill in the art to practice the invention. In order to better enable the reader to understand specific embodiments and the advantages thereof, reference to the following non-limiting examples is suggested. However, the following examples should not be read to limit the scope of the invention.

EXAMPLE 1

Preparation of Liposomes

Liposomes with guest materials encapsulated therein are prepared, according to the general procedure for preparing liposomes recommended by Avanti Polar Lipids, Inc. The general elements of the procedure involve preparation of the lipid for hydration, hydration with agitation, and sizing to a homogeneous distribution of vesicles.

Preparation of lipid for hydration: POPC (1-Palmitoyl-2-Oleoyl-Sn-Glycero-3-Phosphocholine) and negatively charged POPG (1-Palmitoyl-2-Oleoyl-Sn-Glycero-3-[Phospho-rac-(1-Glycerol)] (POPC:POPG=7:3) are dissolved and mixed in chloroform. Once POPC and POPG are thoroughly mixed in an organic solvent, the solvent is removed to yield a lipid film. For small volumes of organic solvent (<1 mL), the solvent may be evaporated using a dry nitrogen or argon stream in a fume hood. For larger volumes, the organic solvent should be removed by rotary evaporation yielding a thin lipid film on the sides of a round bottom flask. The lipid film is thoroughly dried to remove residual organic solvent by placing the vial or flask on a vacuum pump overnight. The dried lipid film is redissolved in cyclohexane to form a lipid solution, which is transferred to containers and frozen by placing the containers on a block of dry ice or swirling the container in a dry ice-acetone or alcohol (ethanol or methanol) bath. After freezing completely, the frozen lipid cake is placed on a vacuum pump and lyophilized until dry (1-3 days depending on volume). Dry cakes are stored frozen until ready to hydrate.

Hydration of lipid film/cake: Hydration of the dry lipid film/cake is accomplished simply by adding an aqueous buffer, which contains one or more guest materials to be encapsulated by liposomes, to the container of dry lipid and agitating. After addition of the hydrating buffer, the lipid suspension is agitated vigorously at room temperature for about one hour. The product of hydration is a large, multi-lamellar vesicle (LMV). External guest materials (not encapsulated) are remove by dialysis or gel filtration.

Sizing of lipid suspension: The prepared liposomes are sized to a homogeneous distribution of vesicles by using the lipid extrusion technique, in which a liposome dispersion is forced through a polycarbonate filter having a pore size of about 400 nm to yield particles having a diameter near the pore size of the filter used. Prior to extrusion through the filter, LMV suspensions are underwent five freeze-thaw cycles.

The liposomes with Rhodamine B is prepared according the above-described procedure. The aqueous buffer used in the hydration step is a buffer (pH 8.2) consisting of 0.1M $NaHCO_3$, 1 mM $CaCl_2$, and 1 mM $MnCl_2$ with 0.004 mM Rhodamine B. Absorption and fluorescence spectra of Rhodamine B encapsulated in liposomes are measured.

Absorption spectra show that both Concanavalin A labeled with tetramethylrhodamine isothiocyanate, Con-A-TMR, and dextran labeled with fluorescein isothiocyanate, Dextran-FTIC, can be co-encapsulated in liposomes. The preparation of liposomes containing Con-A-TMR and Dextran-FITC is prepared according to above-described procedure.

EXAMPLE 2

Preparation of Coatings Containing Multiple Layers of Liposomes on a Substrate

This example illustrates a typical LbL coating procedure for forming a coating containing multiple bilayers of liposome and a polyelectrolyte. Negatively charged liposome with Dextran-FITC encapsulated therein is prepared as described in Example 1. External Dextran-FITC (not encapsulated in liposome) is remove by dialysis using Spectra/Por Cellulose Ester membrane MWCO: 3,000,000. Because POPG is negatively charged, positively charged polyelectrolytes poly(diallyldimethylammonium chloride) (PDDA), or polyethyleneimine (PEI) are used in the LbL coating to form on quartz wafers LBL films containing bilayers [polyelectrolyte/liposome (FITC-Dextran)]$_n$. Firstly, the quartz wafers are dipped into a polyelectrolyte solution (pH=4.5) for 7 minutes, and then in a liposome dispersion for 1 hour to form a bilayer of polyelectrolyte/liposome (FITC-Dextran). Such deposition cycle is repeated for n times to fabricate the films of [polyelectrolyte/liposome (FITC-Dextran)]$_n$, where n is the number of adsorption cycles.

Luminescence responses of [PDDA/liposome (FITC-Dextran)]$_n$ and [PEI/liposome (FITC-Dextran)]$_n$ on quartz wafers in aqueous medium buffer (pH=8.2) consisting of 0.1M NaHCO$_3$, 1 mM CaCl$_2$, and 1 mM MnCl$_2$ are measured. The results demonstrate that the amount of the liposome-encapsulated material increases with the number of deposition cycles. However, examination by atomic force microscopy reveals that liposome on a solid substrate can collapse slowly over time. Therefore, it is preferably that polymerized liposomes and liposomes stabilized by polyelectrolytes or inorganic silica or the like are used in the present invention.

EXAMPLE 3

Preparation of Liposome Stabilized by a Layer of Inorganic Silica

Negatively charged liposome with Dextran-FITC and Con-A-TMR encapsulated therein is prepared as described in Example 1. External Dextran-FITC and Con-A-TMR (not encapsulated in liposome) is remove by dialysis using Spectra/Por Cellulose Ester membrane MWCO: 3,000,000. After dialysis, the liposome concentration is estimated to be about $4.4 \times 10^{-3}$ M.

Tetraethyl orthsilicate (TEOS) or tetramethyl orthosilicate (TMSO) is used in the modification of liposome. 0.5 ml of the above-prepared liposome dispersion is diluted to 3.0 ml and then is stirred vigorously at room temperature. Every three hours, about 5.2 µl of TEOS (or 4.1 µl of TMOS) is added into the liposome. A total of about 15.6 µl of TEOS (or about 14.2 µl of TMOS) is added into the diluted liposome dispersion. The molar ratio of TEOS (or TMOS) to liposome is about 32:1. The experiments are carried out at room temperature.

EXAMPLE 4

Preparation of Polymerized Liposome

This example illustrates polymerized liposomes obtained by polymerization inside hydrophobic layer of the liposomes.

Polymerized liposome with dextran-FITC (MW. 2,500,000) entrapped therewithin is prepared by polymerizing polydiacetylene which is solubilized in the hydrophobic layer of liposome. Liposome is prepared according to the procedure described in Example 1. A mixture of 40% (molar ratio) of phospholipids (POPC:POPG=7:3) and 60% polydiacetylene (PDA) is are dissolved and mixed in chloroform. The solvent is removed to yield a PDA-containing lipid film. The lipid film is thoroughly dried to remove residual organic solvent by placing the vial or flask on a vacuum pump overnight. The dried lipid film is redissolved in cyclohexane to form a lipid solution, which is transferred to containers and frozen by placing the containers on a block of dry ice or swirling the container in a dry ice-acetone or alcohol (ethanol or methanol) bath. After freezing completely, the frozen PDA-containing lipid cake is placed on a vacuum pump and lyophilized until dry (1-3 days depending on volume). Dry cakes are hydrated with a phosphate sodium (PBS) buffer (0.1 M, pH 7.2) containing dextran-FITC (lipid/dextran=100:3 wt). After addition of 0.1 M PBS buffer, the lipid suspension is sonicated at 70° C. for 2 hours. The vesicle dispersion is then cooled and kept at 4° C. overnight. Polymerization is initiated by UV irradiation for at least 60 minutes to obtain a dispersion of polymerized liposome.

EXAMPLE 5

Preparation of Coatings Containing Multiple Layers of Polymerized Liposome on a Substrate The polymerized liposome dispersion prepared in Example 4 is used to prepare coatings containing multiple layers of polymerized liposome on a substrate, according to the procedure described in Example 2.

Absorption and fluorescence spectra of a composite material comprising a quartz wafer and a coating having multiple bilayers of polymerized liposome and PEI (pH 8) are measured in 0.1 M PBS buffer (pH 7.2). The results show that the absorbance and fluorescence intensity of FITC increases with the numbers n of the deposition cycles. Examination with AFM of the composite material confirms that polymerized liposome can be deposited on the surface of the substrate.

What is claimed is:

1. A contact lens, comprising:
a hydrogel bulk material, and
a coating having at least one layer of a vesicle having surface charges and one layer of a polyionic material having charges opposite the charges of the vesicle,
wherein said vesicle is selected from the group consisting of a polymerized liposome, a polymerized micelle, a nanocapsule having a multilayered shell of polyelectrolytes, a microcapsule having a multilayered shell of polyelectrolytes, and combinations thereof, said vesicle encapsulates a guest material selected from the group consisting of a biosensor, a drug, a protein, an amino acid, a nucleic acid, a polypeptide, metallic nanoparticles, magnetic nanoparticles, optically active nanoparticles, and dyes, wherein a first layer in contact directly with the surface of said bulk material is said layer of the polyionic material, or said layer of the vesicle.

2. A contact lens of claim 1, wherein said bulk material is a silicone-containing hydrogel.

3. A contact lens of claim 1, wherein said coating comprises a plurality of bilayers of the vesicle and the polyionic material.

* * * * *